United States Patent [19]

Yamamura et al.

[11] Patent Number: 4,543,253

[45] Date of Patent: Sep. 24, 1985

[54] SOLIDIFIED PHARMACEUTICAL COMPOSITION COMPRISING CELL WALL SKELETON

[76] Inventors: Yuichi Yamamura, 1-9-22, Nikawatakadai, Takarazuka; Ichiro Azuma, 1-2, Aoyamadai, Suita; Katsusuke Ennyu, 2-27, Besshoshinmachi, Takatsuki; Osamu Aoki, 2-3-5-302, Hibarigaoka, Takarazuka, all of Japan

[21] Appl. No.: 930,409

[22] Filed: Aug. 2, 1978

[30] Foreign Application Priority Data

Aug. 9, 1977 [JP] Japan ................. 52-95871

[51] Int. Cl.$^4$ ................. H61K 35/78; H61K 35/66
[52] U.S. Cl. ................. 514/21
[58] Field of Search ................. 424/195, 95

[56] References Cited

U.S. PATENT DOCUMENTS 3,177,117  4/1965  Saunders ................. 424/195

FOREIGN PATENT DOCUMENTS 1164022  2/1964  Fed. Rep. of Germany ...... 424/195

OTHER PUBLICATIONS

Kirk–Othmer, *Encyclopedia of Chemical Technology,* Second Edition, vol. 7, pp. 368–370, (1965), (Kirk–Othmer I).
Kirk–Othmer, *Encyclopedia of Chemical Technology,* Third Edition, vol. 1, pp. 772 and 777, (1978), (Kirk–Othmer II).
Azuma, Gann, 67, pp. 669–677, (1976).
Chemical Abstracts 86:15034p, (1977).
Osol Farrar, Dispensatory of the U.S.A. 25th ed., (1955), Ato Mannitol, p. 784, (Part I).

*Primary Examiner*—Jerome D. Goldberg
*Attorney, Agent, or Firm*—Oblon, Fisher, Spivak, McClelland & Maier

[57] ABSTRACT

A stable, storable pharmaceutical composition is provided which comprises a dehydrated solid mixture of microbial cell wall skeleton, vehicle oil, suspending agent and dispersing agent; wherein said microbial cell wall skeleton has adjuvant and antitumor activity. The composition is easily prepared, stable to long term storage, and easily reconstituted to form a homogeneous suspension which retains high potency.

8 Claims, No Drawings

SOLIDIFIED PHARMACEUTICAL COMPOSITION COMPRISING CELL WALL SKELETON

BACKGROUND OF THE INVENTION

1. Field of the Invention

This invention relates to a solidified pharmaceutical composition comprising microbial cell wall skeleton which has potent adjuvant and antitumor activities.

More particularly, this invention relates to a solidified pharmaceutical composition comprising microbial cell wall skeleton, a vehicle oil, a suspending agent and a dispersing agent, which is useful as an immunotherapeutic agent for human tumors, and to a method for preparing the same.

2. Description of the Prior Art

It was reported that the cell wall skeleton (hereinafter referred to as "CWS") derived from microorganisms such as the genus Mycobacterium (e.g. *Mycobacterium bovis* BCG), Nocardia (e.g. *Nocardia rubra*) or the like has adjuvant and antitumor activities. However, since the CWS is a water-insoluble substance, it could not be administered in a form of conventional aqueous injection preparation to human body, and accordingly, for effective administration to human body for therapy, it was indispensable to apply it in a form of suspension, and the CWS was formulated as an oil-attached form and then made into oil-in-water suspension as an effective preparation for use. For example, it was reported that the CWS of *Mycobacterium bovis* BCG, which was treated with a mineral oil (e.g. Drakeol 6 VR) and suspended in saline-0.2% Tween 80 (trade name) was effective for the suppression of tumor growth or regression of established tumor in animals [I. Azuma et al, Gann (cancer), 65, 493–505(1974); T. Yoshimoto et al, Gann (Cancer), 67, 441–445(1976) and B. Zbar, et al J. Nath. Cancer Inst., 52, 1571–1577(1974)], and such oil-attached BCG CWS was effective for the prolongation of survival period and improvement of immunological status of tumor-bearing patients [Y. Yamamura, et al, Gann (Cancer), 67, 669–677 (1976), Y. Yamamura, et al, Gann (Cancer), 66, 355–363 (1975) and K. Yasumoto, et al, Gann (Cancer), 67, 787–795 (1976)].

As explained above, although the oil-attached CWS has many advantages in the aspects of complication and quality control as immunotherapeutic agents in comparison with living microorganisms, there were problems with its use in that suspensions of oil-attached CWS were unstable and unable to keep at the same condition more than a day so that the preparations deteriorated in quality and trended to decrease of the potency of activities thereof. Accordingly, it has been needed to prepare said suspension of oil-attached CWS every time immediately before use, i.e. administration to patients, but, since this is very complicated and inconvenient for therapy, it has been substantially impossible to use such suspension preparation for practical therapy in the required location in the hospital.

SUMMARY OF THE INVENTION

In order to overcome the disadvantages of the suspension preparation of the oil-attached CWS as stated above so that it may be used effectively and practically in hospital, one object of this invention is to provide stable preparations of the oil-attached CWS which can be kept without loss of the potency of activities thereof for a long term. Another object of the invention is to provide the solidified composition of the oil-attached CWS which is stable and ideal to meet the industrial manufacture and the usage in hospital.

Briefly, these objects and other objects of the invention as hereinafter will become more readily apparent can be attained by providing a solidified pharmaceutical composition which comprises microbial CWS, vehicle oil, suspending agent and dispersing agent, and can be prepared by lyophilizing a suspension of the CWS, vehicle oil, suspending agent and dispersing agent.

DETAILED DESCRIPTION OF THE PREFERRED EMBODIMENT

The CWS to be used in this invention is one derived from microorganisms such as the genus Nocardia (e.g. *Nocardia rubra, Nocardia paraffinica, Nocardia asteroides*, etc.), Mycobacterium (e.g. *Mycobacterium bovis*, etc.), Corynebacterium (e.g. *Corynebacterium diphtheriae*, etc.), Arthrobacter (e.g. *Arthrobacter paraffineus*, etc.), or the like.

And, the CWS to be used in this invention can be prepared by fractionating and purifying cell walls from cells of the cultured bacteria in a conventional manner [I. Azuma, et al, J. Nath. Cancer Inst., 52, 95 (1974) and I. Azuma, et al, Biken J., 18, 1 (1975))]. An example of such a preparation of the CWS is given later in this discussion.

The vehicle oil to be used in this invention is intended to mean an oil having an ability to stimulate the adjuvant and antitumor activities. Said vehicle oil may include natural and synthetic or semisynthetic oil, such as those exemplified in Immunology, 27, 311–329 (1924), preferably, an animal oil [e.g. squalene, vitamin A oil, vitamin E oil, ubiquinone, etc., and a metabolite thereof, a plant oil [e.g. miglyol, AD-65 (Trade name, a mixture of peanut oil, aracel and aluminum monostearate), etc.], synthetic or semisynthetic oil thereof [e.g. squalane, vitamin A palmitate, etc.], mineral oil [e.g. liquid paraffin, Bayol F (Trade name), Drakeol 6VR (Trade name, Pennsylvania Refining Co.), etc.], and the like, and more preferably squalene, squalane, miglyol, Drakeol 6VR and vitamin A palmitate. As to the vehicle oil as illustrated above, it is to be noted that such oils are effective and useful to stimulate the transportation of the CWS to the region (e.g. the thymus cell region), to make the CWS remain in the region for fairly long time and to promote the immunizing ability thereof.

Among such vehicle oil as exemplified hereinabove, the animal oil, especially such as squalene can preferably be used in this invention since such a vehicle oil is derived from a natural source and accordingly has an affinity for the living human body.

The suspending agent to be used in this invention may include a conventional emulsifying agent such as a hydrocarbon (e.g. powdered acacia gum, traganth powder, agar, pectic substances, sodium alginate, methylcellulose, carboxymethylcellulose, etc.), protein or phospholipid (e.g. deutoplasm, casein, gelatin, lecithin, etc.), polyalcohol ester (e.g. polyoxyethylenesorbitan-monolaurate (Tween-20), -monopalmitate (Tween-40), -monostearate (Tween-60), -monooleate (Tween-80), sorbitan-monolaurate (Span-20), -monopalmitate (Span-40), -monostearate (Span-60), -monooleate (Span-80), etc.) and the like, among which polyalcohol ester can preferably be used in this invention, and especially polyoxyethylene-sorbitan ester such as polyoxyethylenesorbitan monooleate is more preferably used.

Preferred examples of the dispersing agent to be used may include sugar and sugar alcohol such as glucose, mannitol, sorbitol or the like, preferably sugar alcohol and more preferably mannitol.

As to effectiveness of the dispersing agent contained in the solidified pharmaceutical composition, it is to be noted that said agent is useful for the purpose of not only making the reconstitution thereof into suspension easier, but also making the reconstituted suspension isotonic.

The ratio of each component contained in the solidified composition of this invention (i.e. CWS, vehicle oil, suspending agent and dispersing agent) may optionally be determined, and preferred and reasonable ratio thereof will be apparent from the working Examples described below.

The solidified pharmaceutical composition can be prepared, for example, by suspending a mixture of each component as mentioned above in a conventional manner and lyophilizing the thus prepared suspension. More particularly, for example, the CWS is placed in a tissue homogenizer and the vehicle oil is added thereto where, if desired, the mixture is ground to a smooth paste; to the mixture, there is added dropwise an aqueous solution of dispersing agent containing a suspending agent and the mixture is ground and homogenized to provide a uniform suspension, and then the thus prepared suspension is transferred into a vial, frozen rapidly using, for example, liquid nitrogen and lyophilized.

The solidified pharmaceutical composition prepared according to this invention can be used by resuspending it by the addition of sterilized water before administration to patients, and has the following advantages.

(1) The solidified pharmaceutical composition of this invention can be preserved for a much longer term as compared with the fresh-prepared suspension of the oil-attached CWS, keeping not only its physical stability, but also potency of the activities substantially unchanged.

In this connection, it is to be noted that the fresh-prepared suspension of the oil-attached CWS usually decomposes after about one hour to a non-uniform and uneven suspension, which is difficult to reconstitute in to a uniform suspension, and which therefore may result in not demonstrating the original therapeutic effectiveness of the CWS per se after the lapse of a longer period of the preservation thereof.

(2) Using the solidified pharmaceutical composition of this invention, a uniform suspension of the oil-attached CWS can easily be reconstituted, which is highly stable in the same state as the fresh-prepared suspension, by simple addition of sterilized water thereto even after the lapse of longer term of the preservation thereof, and said resuspended preparation can exhibit the same activity as that of the fresh-prepared suspension of the oil-attached CWS and can demonstrate the higher therapeutic effectiveness of CWS per se than the suspension of the oil-attached CWS preserved for a long term, as mentioned above.

(3) In the past time, the suspension of the oil-attached CWS was prepared every time just before administration as mentioned above. On the other hand, since a single dose of the CWS is very small amount (e.g. about 100–300 μg) and accordingly the operation to prepare the suspension of the oil-attached CWS is very troublesome, it is very difficult to prepare the suspension of the same quality comprising the given amount. Even if larger amount of the suspension of the oil-attached CWS is prepared at once in order to overcome these defects, the suspension per se is very unstable and can not be kept for a long term as mentioned before, and therefore most of the suspension can not be therapeutically used and is thrown away. However, according to this invention, it is easy and possible to produce the solidified composition comprising the given small amount of the oil-attached CWS on a large scale, and to control the product quality.

With regard to the higher stability and higher potency of the activities of the suspension reconstituted from the solidified composition of this invention, as explained as one of the inventive merits or unexpected and surprising properties hereinabove, it is to be understood that such preserved higher stability and potency seem to be attributable to the fact that the oil-attached CWS can be homogeneously dispersed in such a reconstituted suspension and the dispersed oil-attached CWS can be present in fine globules (e.g. around 5μ in diameter) without agglutination thereof to larger particles.

As seen from the above explanation of this invention, it is to be noted and emphasized that as a result of this invention, it is no longer difficult or impossible to provide an oil-attached CWS anti-tumor agent in good quality on an industrial scale. Rather, it is now not only possible but easy and accordingly, efficient use of the CWS in hospitals is facilitated. This fact is epochal and means that this invention will be a boon to the cancer patients.

Having generally described this invention, a further understanding can be obtained by reference to certain specific examples which are provided herein for purposes of illustration only and are not intended to be limiting unless otherwise specified.

MATERIALS AND METHODS

Adjuvants

The preparation of the CWS of *Nocardia rubra* (hereinafter referred to as *N. rubra*) is described above.

Drakeol 6VR (Pennsylvania Refining Co., Butler, U.S.A.), squalene (Tokyo Kasei Co., Ltd., Japan) and squalane (Katayama Kagaku Co., Ltd., Japan) were used as oils for the preparation of oil-attached CWS of *N. rubra*.

Antigens m-[4(4'-monophenylazo)-phenyl]-N-acetyl-L-tyrosine (ABA-N-acetyl-tyrosine) and ABA-bacterial α-amylase (ABA-BαA) were prepared by the method described in *J. Biol. Chem.*, 238, 1726–1730 (1959). Bacterial α-amylase (Liquefying Type, Lot No. E5X01) purified from *Bacillus subtilis* was purchased from Seikagaku Kogyo Co., Ltd. Japan.

Tumors

Leukemia EL4 of C57BL/6J mice, mastocytoma P815-X2 of DBA/2 mice, Meth A of BALB/c mice, fibrosarcoma induced by 3-methylcholanthrene in C57BL/6J mice designated MC104 were used. EL4, mastocytoma P815-X2 and Meth A were maintained serially by the passage of ascites in respective syngeneic female mice. MC104 was passaged serially by the subcutaneous transplantation in syngeneic mice.

Mice

The mice, six- to eight-week-old female mice of BALB/c, C578BL/6J and DBA/2 were obtained from Shizuoka Jikken Dobutsu Nokyo, Shizuoka, Japan. The animals were given food (from Oriental Yeast Ind., Japan) and water freely.

Medium Solution

Eagle's minimal essential medium (MEM) containing 100 U/ml of penicillin and 100 μg/ml of streptomycin was obtained from the Research Foundation for Microbial Diseases, Osaka University, Japan. Medium RPMI-1640 for tissue culture was obtained from Nissui Seiyaku Co., Ltd., Japan. Fetal calf serum (Lot No. 4055722) was purchased from Flow Laboratories (Rockville, U.S.A.) and was inactivated by heating at 56° for 30 min before use.

Direct Cytotoxicity Test

A tumor cell (Meth A) suspension in MEM solution was mixed with an equal volume of oil-attached CWS or oil droplets and kept in ice-cold water bath for 60 min. The viability of the tumor cells was determined by Eosin Y exclusion test.

Determination of Adjuvant Activity on the Induction of Delayed Type Hypersensitivity Guinea pigs were given primary immunization into four foot pads with a total of 50 μg of ABA-N-acetyltyrosine with or without the CWS of N.rubra in various vehicle oils as water-in-oil emulsion. Two weeks later, skin test with 100 μg of ABA-BαA was carried out and the reaction was measured at 24 and 48 hr after intradermal injection of test antigen.

Cell-mediated Cytotoxicity Test

C57BL/6J mice ($H-2^b$) were immunized intraperitoneally with viable cells of mastocytoma P815-X2 ($H-2^d$) with or without oil-attached CWS of N. rubra. The eleventh days after immunization, the cell-mediated cytotoxicity assay was carried out by using the spleen cells of immunized mice and $^{51}Cr$-labeled mastocytoma P815-X2 cells by the method of Brunner et al [Immunology, 18, 501–515 (1970)] with some modifications. [T Taniyama et al, Jpn. J. Microbiol 19, 255–264 (1975)]. The ratio of spleen cells (effector cells) to $^{51}Cr$-labeled mastocytoma P815-X2 cells (target cells) was 100:1. Target cell-lysis was expressed as percent of specific target cell-lysis according to the following formula: Percent of specific target cell-lysis = Release of specific target cell-lysis/Maximal release-spontaneous release × 100 Maximal chromium release was measured by complete cell-lysis where target cells alone were frozen-and-thawed twice.

Preparation of oil-attached CWS of N. rubra

The solidified preparation of the CWS of N. rubra was prepared as described in the following working Examples.

RESULTS

Effect of the CWS of N. rubra Treated with Various Oils on Cell-mediated Cytotoxicity in Allogeneic Mice The CWS of N. rubra was treated with squalene or Drakeol 6VR and suspended in 0.9% saline solution containing 0.2% Tween 80 solution. C57BL/6J mice were immunized with a mixture of mastocytoma cells and adjuvants as described above. As shown in Table I, the preparations of CWS of N. rubra treated with Drakeol 6VR-saline, squalene-saline or squalene-mannitol were clearly effective as adjuvant for the induction of effector cells in the spleen of allogeneic mice. It was also shown that the lyophilized adjuvants which were resuspended by the addition of sterilized water before use were as effective as the adjuvants freshly prepared before use.

Direct Cytotoxicity to Tumor Cells

As shown in Table II, all the preparations tested containing the CWS of N. rubra showed no cytotoxicity when these adjuvants and tumor cells (Meth A from BALB/c) were kept in ice-water bath for 60 min., however, lyophilized preparation of squalene-0.9% saline solution containing 0.2% Tween 80 showed some toxicity to tumor cells. Freshly prepared preparation was not cytotoxic in the same condition. However, the lyophilized preparation of the CWS of N. rubra treated with squalene-mannitol was not cytotoxic.

Antitumor Activity of Oil-attached N. rubra CWS

The antitumor activity of N. rubra CWS treated with squalene, squalane or Drakeol 6VR and suspended in 5.6% mannitol solution containing 0.2% Tween 80 was tested using transplantable tumors in syngeneic mice. As shown in Table III, IV, V and VI, the preparations of N. rubra CWS treated with various kinds of oils were shown to have nearly the same activity for the suppression of tumor growth of EL-4 leukemia, Meth A and MC104 in respective syngeneic mice. As shown in Table III, suppression activity of the CWS of N. rubra on the growth of Meth A in BALB/c mice was found not to be different between freshly prepared-Drakeol-saline preparation and the squalene-mannitol or squalane-mannitol preparations which were lyophilized and suspended with sterilized water before use.

Efficacy of Oil Composition on Delayed Type Hypersensitivity in Guinea Pigs

The CWS of N. rubra was suspended in the mixture of oil (such as Drakeol 6VR, squalene or squalane) and Arlacel A at the ratio of 85:15 and then mixed together with a solution of ABA-N-acetyltyrosine with or without the CWS of N. rubra as water-in-oil emulsion. Guinea pigs were immunized by the intramuscular injection of above mixture of adjuvant and antigen. Two weeks later, the skin test with ABA-BαA was carried out and the skin reaction was read at 24 and 48 hr after intradermal injection of test antigen. As shown in Table VII, positive skin reaction to ABA-BαA was observed in guinea pigs which were immunized with ABA-N-acetyltyrosine together with the CWS of N. rubra and squalene or squalane as well as Drakeol 6VR as water-in-oil emulsion.

The test data are shown in the following tables.

TABLE I

Effect of Oil-attached N. rubra CWS on Cell-mediated Cytotoxicity to Mastocytoma P815-X2 in C57BL/6J Mice

| Mice were immunized with: | Specific target cel-lysis (%) | |
|---|---|---|
| | Exp. 1[a] | Exp. 2[b] |
| Mastocytoma P815-X2 cells (1 × 10⁴) | | |
| +N. rubra CWS-squalene-mannitol | 64.2 | 41.1 |

TABLE I-continued

Effect of Oil-attached *N. rubra* CWS on Cell-mediated Cytotoxicity to Mastocytoma P815-X2 in C57BL/6J Mice

| Mice were immunized with: | Specific target cell-lysis (%) | |
|---|---|---|
| | Exp. 1[a] | Exp. 2[b] |
| +*N. rubra* CWS-Drakeol 6VR-mannitol | — | 58.3 |
| +*N. rubra* CWS-squalene-saline | 50.4 | — |
| +*N. rubra* CWS-Drakeol 6VR-saline | 26.9 | 28.4 |
| +Squalene-mannitol | 8.2 | 14.1 |
| +Drakeol 6VR-mannitol | — | 8.7 |
| +Squalene-saline | 2.3 | — |
| +Drakeol 6VR-saline | 0.7 | 16.8 |
| Mastocytoma P815-X2 cells ($3 \times 10^7$) alone | 87.9 | 67.5 |

Note:
Three of C57BL/6J mice in each group were immunized intraperitoneally with a mixture of mastocytoma cells and oil-attached CWS of *N. rubra*. Eleven days later, cell-mediated cytotoxicity was determined by the incubation of spleen cells from immunized mice and $^{51}$Cr-labeled mastocytoma cells at a ratio of 100:1 for 20 hrs. All assays were set up in duplicate.
[a]Freshly prepared adjuvants were used.
[b]Lyophilized materials were resuspended by the addition of sterilized water before use.

TABLE II

Direct Cytotoxicity to Tumor Cells (Meth A) of Oil-attached *N. rubra* CWS In Vitro

| Tumor cells were mixed with: | Concentration of CWS of *N. rubra* | Viability (%) | |
|---|---|---|---|
| | | Freshly Prepared | Lyophilized |
| *N. rubra* CWS-squalene-mannitol | 2 mg/ml | 90.0 | 89.7 |
| | 0.4 mg/ml | 88.8 | 85.0 |
| *N. rubra* CWS-squalene-saline | 2 mg/ml | 92.3 | 87.0 |
| | 0.4 mg/ml | 87.9 | 91.7 |
| *N. rubra* CWS-Drakeol 6VR-saline | 2 mg/ml | 86.7 | 85.8 |
| | 0.4 mg/ml | 86.4 | 84.7 |
| Oil droplets | | | |
| Squalene-mannitol | — | 83.3 | 87.1 |
| Squalene-saline | — | 75.7 | 45.5 |
| Drakeol 6VR-saline | — | 87.1 | 79.1 |
| MEM | — | 100 | 100 |

Note:
A tumor cell (Meth A from BALB/c mice) suspension ($4 \times 10^7$/ml in MEM) was mixed with oil-attached *N. rubra* CWS or oil droplets and was kept in ice-water bath for 60 min., and then the viability of tumor cells was examined by Eosin Y exclusion test. The table shows the ratios to the viability of tumor cells in MEM solution.

TABLE III

Suppression of Tumor Growth (Meth A) with Oil-attached CWS of *N. rubra* in BALB/c Female Mice

| Preparations | Freshly prepared[a] | Lyophilized[b] |
|---|---|---|
| *N. rubra* CWS (100 μg) treated with: | | |
| Squalene | 10/10 | 9/10[c] |
| Squalene | 9/10 | 10/10 |
| Drakeol 6VR | 10/10 | — |
| Control (oil droplets) | | |
| Squalene | 0/10 | 0/10 |
| Squalane | 0/10 | 0/10 |
| Drakeol 6VR | 0/10 | — |

Note:
A mixture of tumor cells (Meth A, $2 \times 10^5$) and 100 μg of oil-attached CWS of *N. rubra* or oil droplets was inoculated intradermally in female BALB/c mice. The table shows the results 4 weeks after inoculation.
[a]*N. rubra* CWS was treated with various oils and suspended in 0.9% saline containing 0.2% Tween 80. The preparation was made before use.
[b]*N. rubra* CWS treated with various oils was suspended in 5.6% mannitol containing 0.2% Tween 80 and lyophilized. The preparations were resuspended with sterilized water before use.
[c]No. of tumor-free mice/No. of mice tested.

TABLE IV

Suppression of Tumor (Meth A) Growth with Oil-attached CWS of *N. rubra* in BALB/c mice

| Preparations[a] | Experiment number | |
|---|---|---|
| | 0823 | 1108 |
| *N. rubra* CWS (100 μg) treated with: | | |
| Squalene-mannitol | 10/10 | 8/10[b] |
| Squalane-mannitol | — | 10/10 |
| Drakeol 6VR-mannitol | 10/10 | 10/10 |
| Miglyol-mannitol | 10/10 | 10/10 |
| Control (oil droplets) | | |
| Squalene-mannitol | 2/10 | 0/10 |
| Squalane-mannitol | — | 0/10 |
| Drakeol 6VR-mannitol | 0/10 | 0/10 |
| Miglyol-mannitol | 2/10 | 0/10 |
| MEM | 0/10 | 0/10 |

Note:
A mixture of 3-methylcholanthrene-induced fibrosarcoma (Meth A) ($1 \times 10^5$) and 100 μg of oil-attached CWS of *N. rubra* or oil droplets was inoculated intradermally in female mice of BALB/c. The table shows the results 42 days after inoculation.
[a]Lyophilized materials were resuspended with sterilized water before use.
[b]No. of tumor-free mice/No. of mice tested.

TABLE V

Suppression of Tumor (MC104) Growth with Oil-attached CWS of *N. rubra* in female mice of C57BL/6J

| Preparation[a] | Experiment number | |
|---|---|---|
| | 0819 | 1109 |
| *N. rubra* CWS (100 μg) treated with: | | |
| Squalene-mannitol | 6/10 | 10/10 |
| Squalane-mannitol | — | 10/10 |
| Drakeol 6VR-mannitol | 7/10 | 7/10 |
| Miglyol mannitol | 7/10 | 10/10 |
| Control (oil droplets) | | |
| Squalene-mannitol | 0/10 | 0/10 |
| Squalane-mannitol | — | 0/10 |
| Drakeol 6VR-mannitol | 0/10 | 0/10 |
| Miglyol-mannitol | 0/10 | 0/10 |

Note:
A mixture of 3-methylcholanthrene-induced fibrosarcoma (MC104) ($1 \times 10^6$) and 100 μg of oil-attached *N. rubra* CWS or oil droplets was inoculated intradermally in female mice of C57BL/6J. The table shows the results 42 days after inoculation.
[a]Lyophilized materials were resuspended with sterilized water before use.
[b]No. of tumor-free mice/No. of mice tested.

TABLE VI

Suppression of Tumor (EL-4 leukemia) Growth with Oil-attached CWS of *N. rubra* in female C57BL/6J mice

| Preparations[a] | Experiment number | | |
|---|---|---|---|
| | 0824 | 0830 | 0907 |
| *N. rubra* CWS (100 μg) treated with: | | | |
| Squalene-mannitol | 8/10 | 9/10 | 7/10[b] |
| Drakeol 6VR-mannitol | 5/10 | 7/10 | 5/10 |
| Miglyol-mannitol | 4/10 | 8/10 | 8/10 |

TABLE VI-continued

Suppression of Tumor (EL-4 leukemia) Growth with Oil-attached CWS of *N. rubra* in female C57BL/6J mice

| Preparations[a] | Experiment number | | |
|---|---|---|---|
| | 0824 | 0830 | 0907 |
| Control (oil droplets) | | | |
| Squalene-mannitol | 0/10 | 0/10 | 0/10 |
| Drakeol 6VR-mannitol | 0/10 | 0/10 | 0/10 |
| Miglyol-mannitol | 0/10 | 0/10 | 0/10 |
| MEM | 0/10 | 0/10 | 0/10 |

Note:
A mixture of EL-4 leukemia cells (1 × 10$^5$) and 100 μg of oil-attached CWS of *N. rubra* or oil droplets was inoculated intradermally in C57BL/6J female mice. The table shows the results 28 days after inoculation.
[a]Lyophilized materials were resuspended with sterilized water before use.
[b]No. of tumor-free mice/No. of mice tested.

TABLE VII

Effect of Oil Composition on Delayed Type Hypersensitivity to ABA-N—acetyltyrosine in Guinea Pigs

| Guinea pigs were immunized with ABA-N—acetyltyrosine together with: | Skin reaction to ABA-bacterial α-amylase |
|---|---|
| *N. rubra* CWS (100 μg) | |
| in Drakeol 6VR-Arlacel A (85:15) | 23.4 ± 0.8$^{mm}$    25.7 ± 0.7$^{mm}$a |
| in Squalene-Arlacel A (85:15) | 20.1 ± 1.3    17.9 ± 1.0 |
| in squalane-Arlacel A (85:15) | 18.9 ± 0.5    16.6 ± 0.6 |
| Control [Drakeol 6VR-Arlacel A (85:15)] | 0    0 |

Note:
Five guinea pigs in each group were immunized with 50 μg of ABA-N—acetyltyrosine with or without 100 μg of CWS of *N. rubra* suspended in various kinds of oil vehicles as water-in-oil emulsion. Two weeks after immunization, skin test with 100 μg of ABA-bacterial α-amylase was made.
a Average skin reaction (induration, mm in diameter) ± standard error.

The *Nocardia rubra*-CWS used in the following examples was prepared as follows.

*Nocardia rubra* was cultured in a medium containing polypeptone (2%) and yeast extracts (1%) (pH 7.0) at 30° C. for 3 days, and the cultured broth (18 l) was filtered. Wet mycel (ca. 400 g) was suspended in water (1 l) and ground with Dynomill (0.1-0.2 mm beads; 3,000 rpm; 2 l/hr.) three times. The resultant substance was bufferized (pH 7.5), treated with nucleicacidase (DNase and RNase) for 30 minutes and then centrifuged (800×g, 15 min.). The supernatant was separated and further centrifuged (10,000-20,000×g, 30 min.). The precipitates were collected and suspended in acetone (1 l) and stirred for 24 hours. The precipitates were collected by filtration, suspended in 2% Tritone X-100 (1 l), stirred for 24 hours and then centrifuged (10,000-20,000×g, 30 min.). The precipitates were treated again with Tritone X-100 in the same manner as above. The resultant precipitates were washed with a mixture (1 l) of ethanol and water (1:1) and then with water (1 l) twice, and centrifuged (10,000-20,000×g, 30 min.). The precipitates were suspended in Veronal buffer (pH 9.5), treated with Pronase (50 mg) with stirring at room temperature for 24 hours, and then centrifuged (10,000-20,000×g, 30 min.). The precipitates were washed with water (1 l) three times and centrifuged (10,000-20,000×g, 30 min.). The precipitates were washed with a mixture (1 l) of diethyl ether and ethanol (1:1), dried under reduced pressure at room temperature for 3 days, pulverized and then sieved (125μ) to give fine powder of *N. rubra* CWS (ca. 7 g).

The solidified composition of this invention is resuspended in sterilized water and administered to patients intrapleurally, intralesionally, intradermally, subcutaneously, intramuscularly or intraperitoneally in a single dose of 10-2,000 μg, preferably 100-300 μg of the CWS.

The following examples are given for illustrating this invention in more detail.

EXAMPLE 1

| *N. rubra* CWS | 4 mg |
|---|---|
| Miglyol | 2 drops |
| 5.6% mannitol solution containing | 0.2% |
| Tween 80 | 1 ml |

The CWS of *N. rubra* (140 mg) was placed in a tissue homogenizer equipped with a Teflon pestle (Takashima Shoten Co., Ltd., Japan). Miglyol (70 drops) was added from 27-gauge injection needle of syringe to the CWS and this mixture was ground to a smooth paste at 1000 rpm. Then 5.6% aqueous solution (35 ml) of mannitol containing 0.2% Tween 80 was added to the paste and the grinding was continued to obtain a uniform suspension of small oil droplets associated to CWS of *N. rubra*. For the preparation of lyophilized material, oil-attached suspension of *N. rubra* CWS was transferred into 35 vials (10 ml volume), frozen rapidly using liquid nitrogen, and then lyophilized at room temperature. One ml of sterilized water was added to lyophilized material to make a suspension before use.

EXAMPLE 2

| *N. rubra* CWS | 4 mg |
|---|---|
| Drakeol-6VR | 2 drops |
| 5.6% mannitol solution containing | 0.2% |
| Tween 80 | 1 ml |

Drakeol-6VR was used instead of the miglyol used in the above Example 1, and the mixture was treated in the same manner as the Example 1 to give a solidified composition.

EXAMPLE 3

| *N. rubra* CWS | 4 mg |
|---|---|
| Squalene | 2 drops |
| 5.6% mannitol solution containing | 0.2% |
| Tween 80 | 1 ml |

Squalene was used instead of the miglyol used in the above Example 1, and the mixture was treated in the same manner as the Example 1 to give a solidified composition.

EXAMPLE 4

| *N. rubra* CWS | 4 mg |
|---|---|
| Vitamin A palmitate | 2 drops |
| 5.6% mannitol solution containing | 0.2% |
| Tween 80 | 1 ml |

Vitamin A palmitate was used instead of the miglyol used in the Example 1 and the mixture was treated in the same manner as the Example 1 to give a solidified composition.

EXAMPLE 5

| | |
|---|---|
| *N. rubra* CWS | 4 mg |
| Miglyol | 2 drops |
| 5.6% glucose solution containing | 0.2% |
| Tween 80 | 4 ml |

5% aqueous solution of glucose was used instead of the 5.6% aqueous solution of mannitol used in the Example 1, and the mixture was treated in the same manner as the Example 1 to give a solidified composition.

We claim:

1. A stable, storable pharmaceutical composition, which comprises a dehydrated solid mixture of *Nocardia rubra* cell wall skeleton, vehicle oil comprising squalene or liquid petrolatum, suspending agent, and dispersing agent comprising mannitol, sorbitol or glucose; wherein said cell wall skeleton has anti-tumor activity; wherein said cell wall skeleton is present in an amount effective to exhibit anti-tumor activity; wherein said vehicle oil is present in an amount less than 8 mg and effective to stimulate the anti-tumor activity of said cell wall skeleton; wherein said suspending agent is present in an amount less than 1 mg and effective for the preparation of an aqueous suspension of said cell wall skeleton and said vehicle oil; and wherein said dispersing agent is present in an amount less than 56 mg and effective to render an aqueous suspension of said cell wall skeleton, said vehicle oil and said suspending agent isotonic.

2. The composition of claim 1, wherein said suspending agent is a polyalcohol ester.

3. The composition of claim 2, wherein said suspending agent is polyoxyethylenesorbitan ester.

4. The composition of claim 1, wherein said vehicle oil is liquid petrolatum, said suspending agent is polyoxyethylenesorbitan ester and said dispersing agent is mannitol.

5. The composition of claim 4, which is prepared by lyophilizing a suspension comprising said cell wall skeleton of *Nocardia rubra*, said liquid petrolatum, said polyoxyethylenesorbitan ester and said mannitol.

6. The composition of claim 1, wherein said vehicle oil is squalene, said suspending agent is polyoxyethylenesorbitan ester and said dispersing agent is mannitol.

7. The composition of claim 6, which is prepared by lyophilizing a suspension comprising said cell wall skeleton of *Nocardia rubra* said squalene, said polyoxyethylenesorbitan ester and said mannitol.

8. The composition of claim 1, which is prepared by lyophilizing a suspension comprising said cell wall skeleton, said vehicle oil, said suspending agent and said dispersing agent.

* * * * *